United States Patent [19]

Verbrugge

[11] Patent Number: 4,554,109
[45] Date of Patent: Nov. 19, 1985

[54] ESTERS OF 1,5-DIMETHYL BICYCLO [3.2.1] OCTAN-8-OL

[75] Inventor: Pieter A. Verbrugge, Amsterdam, Netherlands

[73] Assignee: Shell Oil Company, Houston, Tex.

[21] Appl. No.: 561,754

[22] Filed: Dec. 15, 1983

Related U.S. Application Data

[62] Division of Ser. No. 365,694, Apr. 5, 1982, abandoned.

[30] Foreign Application Priority Data

Jul. 30, 1981 [GB] United Kingdom ................. 8123326

[51] Int. Cl.[4] .................. C07C 141/12; C07C 137/00
[52] U.S. Cl. ............................ 260/457; 260/456 NS; 260/958; 252/33.6
[58] Field of Search .................. 260/457, 456 NS, 958

[56] References Cited

U.S. PATENT DOCUMENTS

| | | | |
|---|---|---|---|
| 4,212,751 | 7/1980 | Schadenberg et al. | 260/958 |
| 4,218,348 | 8/1980 | Mulder et al. | 252/522 R |
| 4,237,322 | 12/1980 | Mulder et al. | 568/820 |
| 4,239,707 | 12/1980 | Mulder et al. | 570/130 |

*Primary Examiner*—Nicky Chan
*Attorney, Agent, or Firm*—Ronald R. Reper

[57] ABSTRACT

Process for the preparation of esters of 1,5-dimethyl bicyclo [3.2.1] octan-8-ol and/or derivatives thereof by reacting 1,5-dimethyl-1,5-cyclooctadiene with an inorganic polybasic acid.

2 Claims, No Drawings

ESTERS OF 1,5-DIMETHYL BICYCLO [3.2.1] OCTAN-8-OL

This is a division of application Ser. No. 365,694, filed Apr. 5, 1982, now abandoned.

BACKGROUND OF THE INVENTION

The present invention relates to a process for the preparation of esters of 1,5-dimethyl bicyclo [3.2.1] octan-8.ol and/or derivatives thereof. The present invention further relates to novel esters of 1,5-dimethyl bicyclo [3.2.1] octan-8-ol and derivatives thereof which may find application as plasticizers, fire retardent agents and which because of their thermal stability, can also be of interest as heat transfer liquids, e.g. in transformer oils, brake fluids, oil additives and in synthetic lubricants. They may also be used in the detergent and textile industry and may serve as precursors for certain aroma chemicals. The present invention relates in particular to the phosphate and sulphate esters of 1,5-dimethyl bicyclo [3.2.1] octan-8-ol.

Esters derived from 1,5-dimethyl bicyclo [3.2.1] octan-8-ol and carboxylic acids are described in Dutch patent application Nos. 7805142 and 7805143, respectively. They can be prepared by reacting 1,5-dimethyl-1,5-cyclooctadiene with the appropriate carboxylic acid, preferably in the presence of an acidic catalyst. It is also possible to prepare such esters by reacting the bicyclic alcohol (1,5-dimethyl bicyclo [3.2.1] octan-8-ol) with the appropriate carboxylic acid in the presence of an acidic ion exchange resin or by transesterification procedures.

It is not known, however, to prepare esters of 1,5-dimethyl bicyclo [3.2.1] octan-8-ol and inorganic acids. It is stated by J. K. Whitesell, R. S. Matthews and P. A. Solomon, Tetrahedron Letters No. 19, pp 1549–1552, 1976 that 1,5-dimethyl bicyclo [3.2.1] octan-8-ol can be obtained in 50% yield by reacting 1,5-dimethyl-1,5-cyclooctadiene with a solution of perchloric acid in a mixture of water and dioxane. No reference is made to the presence of the corresponding perchlorate. When the Applicants tried to prepare a sulphate ester of 1,5-dimethyl bicyclo [3.2.1] octan-8ol by reacting this compound with sulphuric acid, the only result was tarry substance. When phosphoric acid was brought into contact with 1,5-dimethyl bicyclo [3.2.1] octan-8-ol, no reaction was observed, not even at elevated temperature.

It has now surprisingly been found that esters of 1,5-dimethyl bicyclo [3.2.1] octan-8-ol and inorganic acids can be prepared in rather good yields and under very mild process conditions when 1,5-dimethyl-1,5-cyclooctadiene is reacted with an inorganic polybasic acid.

SUMMARY OF THE INVENTION

The present invention therefore relates to a process for the preparation of esters of 1,5-dimethyl bicyclo [3.2.1] octan-8-ol and/or derivatives thereof by reacting 1,5-dimethyl-1,5-cyclooctadiene with an inorganic polybasic acid.

DESCRIPTION OF PREFERRED EMBODIMENTS

Polybasic acids as mentioned herein are defined as acids which possess at least two hydrogen atoms which can be released in an aqueous environment and which have a dissociation constant at room temperature of at least $10^{-4}$ (for concentrations of 0.1 N or below). Examples of inorganic polybasic acids are acids containing sulphur or phosphorus such as sulphuric acid, sulphurous acid, phosphoric acid and phosphorus acid. Preference is given to the use of sulphuric and phosphoric acid.

It has been found that the inorganic polybasic acids can be used in a wide range of concentrations. Good results can be obtained using commercially available concentrated aqueous solutions, e.g. 85% w phosphoric acid and 95–98% w sulphuric acid, but less concentrated aqueous solutions can also be used.

The addition of phosphorus pentoxide to concentrated phosphoric acid (to bind the amount of water present therein) reduced to some extent the rate of reaction between the starting diolefin and phosphoric acid.

If desired, the process according to the present invention can be carried out in the presence of an inert solvent. Examples of suitable solvents comprise ethers especially cyclic ethers such as tetrahydrofuran and dioxane, as well as hydrocarbons such as hexane, heptane, benzene, toluene and xylene and halogenated hydrocarbons such as methylene dichloride, chloroform, carbon tetra chloride and dichlorethane. Good results have been obtained using tetrahydrofuran.

A suitable starting material in the process according to the present invention comprises, apart from 1,5-dimethyl-1,5-cyclooctadiene itself, a mixture consisting of 1,5-and 1,6-dimethyl-1,5cyclooctadiene, which, according to French patent specification 1,283,217 and Dutch patent application No. 7800529, can be obtained by dimerization of isoprene. The presence of 1,6-dimethyl-1,5-cyclooctadiene in the reaction mixture does not interfere with the formation of the desired ester(s) or its separation from the reaction mixture.

The process according to the present invention is generally carried out at temperatures between 0° C. and 100° C., preferably at room temperature or slightly below. It may be necessary to cool the reaction mixture, e.g. when sulphuric acid is used. The ratio of diolefin and polybasic acid is not critical and may vary within wide limits. Equimolar ratios can be applied conveniently but an excess of polybasic acid, for instance up to 5 times the molar amount of diolefin, can also be used.

Depending on the molar ratios applied mono- or polyesters will be obtained. When sulphuric acid is used as the polybasic reagent, normally the disulphate of 1,5-dimethyl bicyclo [3.2.1] octan-8-ol will be obtained. This is a very interesting compound since the sulphate esters can be converted readily into 1,5-dimethyl bicyclo [3.2.1] octan-8-ol by a heat treatment in the presence of an acid. It is thus possible to prepare 1,5-dimethyl bicyclo [3.2.1] octan-8-ol from 1,5-dimethyl-1,5-cyclooctadiene without having to use the rather complex formic acid route as described in Dutch patent application 7805142. The corresponding phosphate was found to be stable under similar conditions. The present invention also relates to novel derivatives of 1,5-dimethyl bicyclo [3.2.1] octane with the general formula

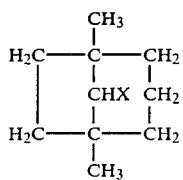

wherein X represents an anion of an inorganic polybasic acid, preferably a group —OPO$_2$H$_2$, —OPO$_3$H$_2$, —OSO$_3$H or -OSO$_2$H or the corresponding salt(s) and di- and tri-esters. The present invention relates in particular to compounds with the general formula I wherein X represents a group —OPO$_3$H$_2$ or a group —OSO$_3$H or the corresponding di- and tri- esters.

It will be appreciated that the products may have the syn- as well as the anti-configuration. Normally mixtures of syn- and anti- monoesters will be formed.

The invention will now be illustrated by means of the following Examples. The compounds prepared have been identified using Infra Red Spectrometry and/or Proton Nuclear Magnetic Resonance Spectroscopy.

EXAMPLE I Dimethyl-1,5-cyclooctadiene (a mixture of 80% w 1,5-dimethyl-1,5 cyclooctadiene and 20% w 1,6-dimethyl-1,5-cyclooctadiene) (27.2 g, 0.2 mol) was placed in a vessel and cooled using an ice bath. Under stirring 96% w sulphuric acid (22.8 g) was added over period of 90 minutes whilst keeping the temperature below 10° C. A brown mixture was obtained which did not rise substantially in temperature when the ice bath was removed. After working up via neutralization with aqueous sodium bicarbonate 23 g of yellow orange neutral liquid was obtained which predominantly consisted of the disulphate of 1,5-dimethyl bicyclo [3.2.1] octan-8 ol (syn/anti-configuration). The infra-red specturm showed the following characteristic absorptions (cm$^{-1}$); 872, 912, 958, 1200, 1374, 1457, 2865 and 2940. The sodium salt of the corresponding mono-ester could be isolated from the aqueous sodium bicarbonate layer.

EXAMPLE II The preparation of the mono-sulphate of 1,5-dimethyl-bicyclo [3.2.1] octan-8-ol was carried out using tetrahydofuran as the solvent. Tetrahydrofuran (25 g) was placed in a vessel cooled with running tap water. Under stirring 96% w sulphuric acid (20 g) was added slowly whilst keeping the temperature below 40° C. A pinkish solution was obtained which was cooled to 23° C. Thereafter dimethyl-1,5-cyclooctadiene (a mixture of 80% w 1,5-dimethyl-1,5 cyclooctadiene and 20% w 1,6-dimethyl-1,5-cyclooctadiene) (14.0 g) was added in 1 g portions. On every addition a rise in temperature (to 30° C.) was observed and the mixture turned dark. No further exotherm was observed after the additon had been completed (90 minutes). Pentane (50 ml) was added followed by the introduction of water (15 ml) under cooling with an ice bath. After settling three layers had been formed, two dark (lower) layers and a yellow (upper) layer.

The combined lower layers were mixed with diethyl-ether (50 ml) and the resulting bottom layer containing mainly sulphuric acid was discarded. The remaining etheral layer was stirred in the presence of sodium sulphate in order dry the layer and to transform remaining sulphuric acid into insoluble sodium bisulphate. After filtering off the strongly acidic solid, the remaining solution was boiled down to give 18.2 g of a slightly brownish oil which on cooling in ether formed crystals. The infra-red spectrum of this compound showed the characteristic absorptions of the mono-sulphate of 1,5-dimethyl bicyclo [3.2.1] octan-8-ol. The slightly yellow upper layer was washed and neutralized with sodium bicarbonate. After drying the mixture, the solvent was evaporated and 5.25 g of the disulphate of 1,5-dimethyl bicyclo [3.2.1] octan-8-ol was obtained. Its infra-red spectrum was identical to that of the product obtained according to Example 1. The mono-ester could be converted into the corresponding mono-ester sodium salt by neutralisation with sodium bicarbonate in ethanol. A white, sticky solid was obtained after evaporation of the solvent.

EXAMPLE III The experiment described in the previous Example was repeated using 13.6 g dimethyl-1, 5-cyclooctadiene (80/20) and 11.6 g sulphuric acid in 20 ml tetrahydrofuran. After the exothermic reaction had subsided 20 ml water was added. A milky emulsion was obtained which broke after slowly heating to 64° C. After distilling off tetrahydrofuran, the remaining mixture was refluxed for three more hours at 100° C. After cooling, the mixture was worked up by adding diethylether, draining off colorless diluted sulphuric acid, and neutralizing with sodium bicarbonate. A light yellow mixture (14.7 g) was obtained comprising 1,5-dimethyl bicyclo [3.2.1] octan-8-ol, the corresponding ether (di(-1,5-dimethyl bicyclo [3.2.1] octyl) ether) and some disulphate of 1,5-dimethyl bicyclo [3.2.1] octan-8-ol. The product mixture was then subjected to a steam distillation which gave 8.85 g product having an infra-red spectrum virtually identical to that of 1,5-dimethyl bicyclo [3.2.1] octan-8-ol. From the bottom product a mixture of 4.25 g of octan-8-ol could be isolated. It was observed that the conversion of the disulphate of 1,5-dimethyl bicyclo [3.2.1] octan-8-ol into the bicyclic alcohol had to be carried out in the presence of an acid.

COMPARATIVE EXAMPLE A

To 140 g 96% w sulphuric acid was added under cooling and vigorous stirring a portion of 50 g 1,5dimethyl bicyclo [3.2.1] octan-8-ol. After the reaction had subsided, the reaction mixture was worked up and analyzed in the usual manner. Virtually no product could be detected, the main products being hydrocarbons.

EXAMPLE IV

Dimethyl-1, 5-cyclooctadiene (a mixture of 80% w 1,5-dimethyl-1,5 cyclooctadiene and 20% w 1,6-dimethyl-1,5-cyclooctadiene (53.2 g) was placed in a vessel and 85% w phosphoric acid (50 g) was added under mechanical stirring. An exothermic reaction occurred and the color of the reaction mixture became orange. The thick emulsion obtained was worked up by adding diethyl-ether (50 ml) and water (25 ml) under stirring. The lower layer, containing phosphoric acid, was discarded and the upper layer neutralized with potassium carbonate. Acidification of the basic solution obtained with hydrochloric acid gave 35 g of an oil which solidified on standing and which contained a mixture of the syn- and anti- mono-phosphate of 1,5-dimethyl bicyclo [3.2.1] octan-8-ol. The syn-isomer could be obtained in a nearly pure state by recrystallization of the product mixture from pentane. Characteristic broad P-OH absorption bands were found in the 1000–1100 cm$^{-1}$ range and characteristic broad P=O absorption bands were found from 1210–1270 cm$^{-1}$. Sharp absorption peaks were measured at 738, 882, 1390 and 1465 cm$^{-1}$, respectively. The monophosphate was also identified by proton magnetic resonance spectrocopy.

EXAMPLE V

The preparation of the mono-phosphate of 1,5-dimethyl bicyclo [3.2.1] octan-8-ol was carried out using tetra-hydrofuran as the solvent. To 20 g 85% w phosphoric acid was added under stirring 6 g of tetrahydrofuran. The temperature reached 35° C. and a pinkish colored mixture resulted. During a period of 38 minutes 14.2 g of dimethyl-1,5-cyclooctadiene (80/20) was added causing a temperature increase to 43° C. After the exothermic reaction had subsided, pentane (50 ml) and water (10 ml) were added. After settling, the lower orange-colored layer (containing excess phosphoric acid and tetrahydorfuran) was separated and discarded. To the remaining layer were added water (40 ml) and slowly sodium bicarbonate. A fluffy white salt was obtained which was taken up in water and acidified with hydrochloric acid. After extraction with diethylether 6.6 g of the mono-phosphate of 1,5-dimethyl bicyclo [3.2.1] octan-8-ol was obtained as a white solid (syn-iomer) could be obtained by working up the filtrate of the diethylether extraction layer, giving a total yield of 9.8 g mono-phosphate. It should be noted that the monophosphate remains stable when heated during one hour in water at 100° C.

EXAMPLE VI

The experiment described in the previous Example was repeated using enough phosphorus pentoxide to react away all water present in the phosphoric acid applied. Addition of dimethyl-1,5-cyclooctadiene (80/20) to the mixture of treated phosphoric acid in tetrahydrofuran did not cause an exotherm and reflux for thirty minutes was required to start the reaction. Working up in the usual manner gave 9.85 g of an oily mixture of monophosphate (syn- and anti-isomer).

COMPARATIVE EXAMPLE B

To a mixture of 85% w phosphoric acid (8 g) and water (4 g) in tetrahydrofuran (20 ml) was added dimethyl-1,5-cyclooctadiene (80/20) (14 g). No conversion was observed, not even when heating the mixture under reflux conditions during two hours.

EXAMPLE VII

The preparation of the mono-phosphite of 1,5-dimethyl bicyclo [3.2.1] octan-8-ol was carried out by firstly preparing phosphorous acid in situ by adding under stirring and cooling the required amount of water (10.1 g) to a mixture of PCl$_3$ (25.6 g) and tetrahydrofuran (25 ml). After the addition of water the tetrahydrofuran solution was refluxed to boil out hydrochloric acid formed during the reaction. The colorless solution was then cooled to ambient temperature and dimethyl-1,5-cyclooctadiene (80/20) (15.2 g) was added during a period of 8 minutes. The temperature increased to 37° C. and the reaction mixture turned pink-yellow. The reaction mixture was stirred for another two hours and then worked up by adding diethylether (50 ml) and water (15 ml). After settling, two layers had been formed. The clear colorless lower layer containing predominantly phosphorous acid and tetrahydrofuran was discarded and the etheral upper layer was stirred with aqueous potassium carbonate (excess). The lower layer obtained was separated from the upper layer which was filtered and acidified with hydrogen chloride. Extraction with diethylether gave 16.3 g of a colorless oil. Infra red absorption bands were observed at (cm$^{-1}$): 660, 735, 765(sh), 1072, 1310–1325, 1452, 2880(sh) and 2930 and 3100–3700.

I claim:

1. Monoester derivative of 1,5-dimethylbicyclo[3.2.1]octane with the general formula

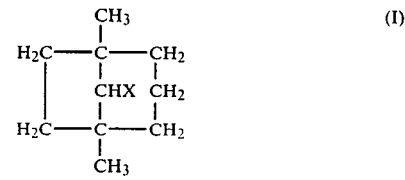

wherein X represents an anion of an inorganic polybasic acid selected from the group consisting of sulfuric acid, and sulfurous acid, and the corresponding sodium salt and diester.

2. Monoester derivative according to claim 1 wherein X represents a group —OSO$_3$H, or the corresponding diester.

* * * * *